United States Patent
Lopath et al.

(10) Patent No.: US 6,808,524 B2
(45) Date of Patent: Oct. 26, 2004

(54) BALLOON ALIGNMENT AND COLLAPSING SYSTEM

(75) Inventors: Patrick David Lopath, Durham, NC (US); Edward Paul Harhen, Duxbury, MA (US)

(73) Assignee: ProRhythm, Inc., Setauket, NY (US)

( * ) Notice: Subject to any disclaimer, the term of this patent is extended or adjusted under 35 U.S.C. 154(b) by 63 days.

(21) Appl. No.: 10/244,271

(22) Filed: Sep. 16, 2002

(65) Prior Publication Data

US 2004/0054362 A1 Mar. 18, 2004

(51) Int. Cl.⁷ .............................................. A61B 18/04
(52) U.S. Cl. .................... 606/27; 623/1.11; 606/194; 604/96
(58) Field of Search ................ 606/27, 194, 198, 606/191, 192; 623/1.11–1.12; 604/96; 607/96–108

(56) References Cited

U.S. PATENT DOCUMENTS

| | | | | |
|---|---|---|---|---|
| 4,338,942 A | * | 7/1982 | Fogarty | 606/194 |
| 4,403,612 A | * | 9/1983 | Fogarty | 606/194 |
| 5,338,295 A | * | 8/1994 | Cornelius et al. | 604/99.04 |
| 5,643,279 A | * | 7/1997 | Trotta | 623/1.11 |
| 5,669,932 A | * | 9/1997 | Fischell et al. | 606/198 |
| 5,776,141 A | * | 7/1998 | Klein et al. | 623/1.11 |
| 5,800,392 A | * | 9/1998 | Racchini | 604/103.01 |
| 5,868,708 A | * | 2/1999 | Hart et al. | 604/104 |
| 5,868,779 A | * | 2/1999 | Ruiz | 606/194 |
| 6,011,995 A | * | 1/2000 | Guglielmi et al. | 607/99 |
| 6,096,054 A | * | 8/2000 | Wyzgala et al. | 606/170 |
| 6,102,908 A | * | 8/2000 | Tu et al. | 606/41 |
| 6,183,492 B1 | * | 2/2001 | Hart et al. | 606/194 |
| 6,355,051 B1 | * | 3/2002 | Sisskind et al. | 606/200 |
| 6,589,274 B2 | * | 7/2003 | Stiger et al. | 623/1.11 |
| 6,607,476 B1 | * | 8/2003 | Barnhart | 600/3 |
| 6,626,861 B1 | * | 9/2003 | Hart et al. | 604/96.01 |
| 2002/0065512 A1 | | 5/2002 | Fjield et al. | |

* cited by examiner

Primary Examiner—Roy D. Gibson
Assistant Examiner—Pete Vrettakos
(74) Attorney, Agent, or Firm—Lerner, David, Littenberg, Krumholz & Mentlik, LLP

(57) ABSTRACT

A balloon catheter is provided with engagement elements disposed within the balloon so that, upon inflation of the balloon, the engagement elements move in the proximal to distal direction of the catheter so as to abut one another and form a substantially rigid column to maintain alignment of the distal end of the balloon with the proximal end of the balloon and with the catheter.

27 Claims, 3 Drawing Sheets

US 6,808,524 B2

BALLOON ALIGNMENT AND COLLAPSING SYSTEM

BACKGROUND OF THE INVENTION

The present invention relates to apparatus incorporating balloons and to techniques employing balloons.

Certain medical and veterinary procedures employ balloons mounted on catheters for various purposes. For example, as described in co-pending, commonly-assigned U.S. patent application Ser. No. 09/905,227, published as U.S. Pat. No. 2002/0065512-A1, the disclosures of which are hereby incorporated by reference herein, a structure including a balloon is used as a reflector for directing ultrasonic energy from an ultrasonic transducer mounted within the balloon onto a region of tissue to be ablated. As further described in the aforementioned application, the balloon structure also focuses the ultrasonic energy. Such a device can be used, for example, to ablate cardiac tissue in treatment of cardiac arrhythmias. Other balloon structures are used for other medical and veterinary procedures.

Typically, the balloon is placed within the body of the subject by threading a carrier catheter having the balloon attached thereto into the body of the subject through the vascular system or other passages within the body and into the desired treatment location with the balloon in a deflated condition. Once the balloon is at the desired location within the subject's body, the balloon is inflated, the desired procedure is performed and the balloon is again deflated and withdrawn by withdrawing the carrier catheter. In many procedures, it is desirable to maintain alignment between portions of the balloon, and to maintain alignment between features of the balloon and the carrier catheter while the balloon is in an inflated condition. For example, in certain preferred embodiments taught in the aforementioned '227 application, the ultrasonic transducer is mounted on a portion of the carrier catheter disposed within the balloon adjacent a proximal end of the balloon. The ultrasonic transducer is generally cylindrical and is coaxial with the carrier catheter. When the balloon is in an inflated condition, the proximal to distal, or lengthwise, axis of the balloon should also be coaxial with the transducer for optimum focusing of the ultrasonic energy.

It would be desirable to provide a rigid reinforcing element which extends between the carrier catheter or ultrasonic transducer and the distal end of the balloon, so as to prevent tilting of the balloon or deformation of the balloon in radial directions, transverse to the lengthwise or proximal to distal direction of the carrier catheter and transducer. However, it is also necessary to allow some flexibility of the balloon in the radial directions when the balloon is deflated to allow threading of the catheter during insertion and withdrawal. The balloon must bend in the radial directions to follow the curves of the vascular system or other body passages.

Some devices which employ balloons also require a passage through the balloon. For example, in many procedures, the threading operation relies on a guide wire which is threaded through the lumen of the carrier catheter and out through the distal end of the structure into the vascular system. After the guide wire is threaded, the catheter, with the balloon thereon, is advanced along the guide wire. In other situations, it may be desirable to introduce structures such as sensing electrodes or other instruments, anchoring elements or the like through the lumen of the catheter and advance these structures so that they project beyond the distal end of the balloon.

Ordinarily, the proximal end of the balloon is affixed to the carrier catheter. As further explained below, the balloon tends to expand in radial directions transverse to the lengthwise direction and to contract in the lengthwise direction when inflated. Thus, the distal end of the balloon should be free to move relative to the carrier catheter in the lengthwise direction during inflation and deflation. Simply providing an extension of the carrier catheter projecting distally through the balloon and through the wall of the balloon at the distal end will not allow for such movement unless a sliding seal is provided at the juncture of the carrier catheter and the distal end. Such a sliding seal increases the bulk of the assembly in the deflated condition and introduces significant reliability issues. Thus, there exists a need for a better structure to provide a lumen or bore extending through the interior of the balloon.

SUMMARY OF THE INVENTION

Apparatus according to one aspect of the present invention includes a balloon having proximal and distal ends and a lengthwise direction between the ends. The balloon has a deflated length between its ends in the deflated condition and an inflated length in an inflated condition, the inflated length being less than the deflated length. Apparatus according to this aspect of the invention also includes a plurality of engagement elements disposed at least partially within the balloon. These elements are moveable with respect to one another in the lengthwise direction. As the balloon contracts in the lengthwise direction upon inflation, the balloon urges the engagement elements into engagement with one another. However, the engagement elements are moveable away from one another in the lengthwise direction upon deflation of the balloon. Apparatus according to this aspect of the invention desirably also includes an axial member extending in the lengthwise direction within the balloon, at least one of the engagement elements being slideable along the axial member to bring the engagement elements into and out of engagement with one another. The axial member most desirably is a flexible member. Most preferably, the axial member includes a spring as, for example, a coil spring, and the spring acts to urge the proximal and distal ends of the balloon away from one another when the balloon is inflated. For example, the engagement element may be small tubular elements surrounding the coil spring.

Most preferably, apparatus according to this aspect of the invention also includes a carrier catheter having a lumen. An end of the balloon, most preferably the proximal end of the balloon, is secured to the carrier catheter. The engagement elements may include a stop member secured to the carrier catheter and disposed within the balloon adjacent the proximal end thereof. The engagement elements desirably include a first or proximal movable engagement element which engages the stop when the balloon is in its inflated condition. Apparatus according to this aspect of the invention allows the balloon to flex in directions transverse to the lengthwise direction of the carrier catheter while the balloon is deflated and while the engagement elements are remote from one another. However, when the balloon is inflated, the engagement elements are forced into engagement with one another so as to provide a rigid support extending lengthwise within the balloon. The support limits or prevents deflection of the distal end of the balloon in the radial directions relative to the proximal end of the balloon and relative to the carrier catheter, thereby maintaining the balloon in alignment with the carrier catheter.

The axial member within the balloon may incorporate a tube. Desirably, the tube is distensible in the lengthwise direction. A proximal end of the tube is mechanically linked to the proximal end of the balloon. For example, the proximal end of the tube may be mechanically connected to the carrier catheter or to the stop, so that the interior bore of the tube communicates with the lumen of the carrier catheter. The distal end of the tube is mechanically linked to the distal end of the balloon. Thus, when the balloon is deflated, the tube is stretched in the lengthwise direction. When the balloon is inflated, the tube is shortened in the lengthwise direction. The tube cooperates with the lumen of the catheter so as to provide a continuous passage extending through the lumen of the catheter and out through the distal end of the balloon. Most preferably, the tube is formed from material as, for example, an expanded polymer, so that the diameter or radial dimensions of the interior bore do not decrease substantially when the tube is stretched in the lengthwise direction. Thus, the continuous passage remains fully functional in all conditions of the balloon. This facilitates use of the assembly with guide wires or other instruments which must protrude beyond the distal end of the balloon.

These and other objects, features and advantages of the present invention will be more readily apparent from the detailed description of the preferred embodiments, set forth below, taken in conjunction with the accompanying drawings.

DETAILED DESCRIPTION

Figure 1:
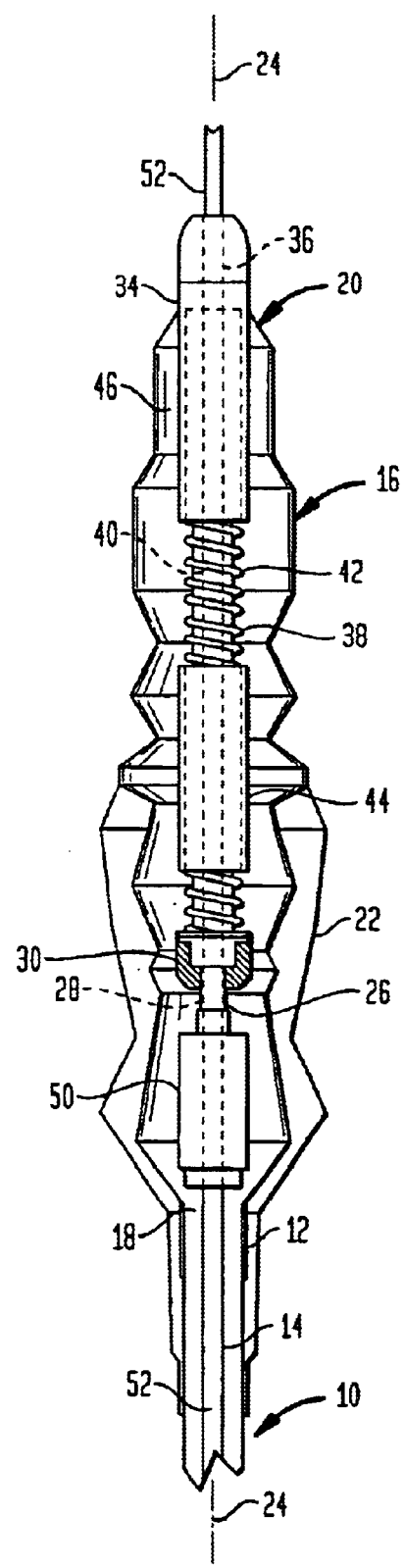
FIG. 1 is a diagrammatic, partially sectional view of a device in accordance with one embodiment of the invention.

Apparatus in accordance with one embodiment of the present invention includes a carrier catheter 10 having a distal end 12 and a proximal end (not shown) remote from the distal end. Ordinarily, the proximal end of the carrier catheter is intended to remain outside of the body, or otherwise accessible to the position for manipulation during the procedure, whereas the distal end is intended to be inserted into the body. Carrier catheter 10 has a central lumen 14. A balloon 16 has a proximal end 18 attached to the distal end of the carrier catheter and has a distal end 20 remote from the proximal end. Balloon 16 is shown in an arbitrary, wrinkled shape representing the balloon in a deflated condition. Balloon 16 desirably is formed from a film which is flexible, but which can form a substantially non-compliant balloon structure when inflated. As explained in the '227 application, materials such as those used to form non-compliant balloons in the angioplasty art such as thin films of polymers such as PET, PETG, nylon, polyurethane and polyethylene can be used. The balloon may be designed for an inflation pressure on the order of a few pounds per square inch to about 12 pounds per square inch or more, most preferably about 8 pounds per square inch, and the balloon wall desirably has the minimum thickness required to withstand the design inflation pressure without rupture as, for example, about 0.001 inches or less and preferably 0.0005 inches or less. Balloon 16 desirably is arranged to form a predetermined shape in the inflated condition (FIG. 2) as, for example, a surface of revolution about a central axis 24 coincident with the central axis of carrier catheter 10 at the distal end 12 thereof, i.e., a generally vertical axis seen in FIG. 1.

An auxiliary balloon 22 surrounds balloon 16 adjacent the proximal end thereof. The auxiliary balloon may be formed from materials similar to those used in the main balloon 16. The central lumen 14 of the carrier catheter, or another lumen (not shown), communicates with the interior of main balloon 16, whereas a different lumen within the carrier catheter (not shown) communicates with the interior of auxiliary balloon 22 so that these balloons may be inflated with different fluids as, for example, an aqueous fluid in the main balloon and air or another gas in the auxiliary balloon. The differences in acoustic impedance between these fluids cause the interface between the main and auxiliary balloons to be highly reflective to ultrasound when the balloons are so inflated.

A rigid, tubular extension 26 is fastened to the distal end of the carrier catheter and extends coaxially with the carrier catheter and with axis 24. Extension 26 has an interior bore 28 continuous with the central lumen 14 of the carrier catheter. A fixed engagement element or stop 30 surrounds the exterior of extension 26 at the distal end of the extension, remote from the carrier catheter within main balloon 16. A hollow, cylindrical nose piece 34 having an interior bore 36 open at the distal end of the nose piece (the upper end seen in FIG. 1) is attached to the distal end 20 of the balloon. Nose piece 34 may be formed from a substantially rigid material as, for example, a metal. The balloon wall may be fastened to the nose piece by an adhesive (not shown).

A flexible, distensible tube 38 having an interior bore 40 extends between stop 30 and nose piece 34. The proximal end of the tube is fastened to the stop 30 and, hence, to extension 26, carrier catheter 10 and the proximal end 12 of the balloon, whereas the distal end of the tube is fastened to the nose piece. The interior bore 40 of tube 38 communicates with the bore 36 in the nose piece and with the bore 28 within extension 26, so that the extension 26, tube 40 and nose piece 36 cooperatively define a continuous passage communicating with the central bore 14 of the carrier catheter and extending through the interior of balloon 16, this passable opening to the exterior of the main balloon 16 at the distal end 20 of the main balloon. Tube 38 desirably is formed from a material such as an expanded polymer as, for example, expanded polytetraflourethylene ("PTFE") or expanded polyethylene. Where the expanded polymer itself is porous, the tube may have a very thin covering of a deformable, nonporous material such as an elastomer. Expanded PTFE tubes sold by Impra, Inc., a subsidiary of C. R. Bard, Inc., of Tempe, Ariz., USA, and commonly employed as a vascular graft material may be employed. Tubes formed from the preferred materials have the property that the interior bore of the tube does not substantially contract in radial directions, transverse to the lengthwise direction along the axis of the tube, when the tube is stretched in the lengthwise direction. Although the present invention is not limited by any theory of operation, it is believed that this property results from the low Poisson's ratio of the material constituting the tube wall. Desirably, when the tube is stretched to the elongated state depicted in FIG. 1, with the balloon fully deflated, the interior diameter of the tube does not vary by more than about 20 percent of the nominal interior diameter, i.e., the diameter of the tube in an axially-shortened, fully inflated condition as depicted in FIG. 2. Most typically, the tube and the interior bore are circular in cross-section. Thus, the diameter of the interior bore is simply the dimension of the interior bore in any direction transverse to the axial direction of the tube. If the tube has a non-circular cross-section, the diameter of the interior bore can be considered as the largest dimension in any direction transverse to the axial direction. Typically, the interior bore has a nominal diameter of about 0.8–1.2 mm and does not vary by more than about 0.2 mm as the tube is stretched throughout the normal operating range, from the fully inflated condition to the fully deflated condition. Further, tubes formed from the preferred expanded polymer materials tend to resist collapse when subjected to external pressure. The most preferred materials, such as expanded PTFE, also have a low coefficient of friction which further facilitates passage of guidewires and other elements through the tube. Moreover, as further discussed below, the tube is stretched by the action of a coil spring during operation of the device. The preferred materials offer very low resistance to stretching.

In one embodiment the tube is formed from expanded PTFE, has a nominal interior diameter of 0.038 inches (0.97 mm) in the unstretched condition, and when stretched by about 30–35% of its unstretched length, has an interior diameter sufficient to pass a guide wire of 0.035 inches (0.89 mm) diameter. In the unstretched condition, even when subjected to an external pressure of 8 pounds per square inch, the tube will pass the same guide wire.

A cylindrical coil spring 42 surrounds tube 38 and extends between stop 30 and nose piece 34. The ends of the spring are secured to stop 30 and nose piece 34. The coil spring is generally cylindrical and is coaxial with tube 38. Thus, the coil spring 42 and tube 38 form a composite axial member extending generally in the lengthwise direction within main balloon 16. In one embodiment, spring 42, in its relaxed condition, is about 28–30 mm long.

A first or proximal mobile engagement element 44 in the form of a thin-walled, hollow cylinder surrounds coil spring 42 and tube 38. In the deflated condition of main balloon 16 illustrated in FIG. 1, the proximal engagement element 44 is slideable on the coil spring and can move proximally and distally from the position shown. A second or distal mobile engagement element 46 surrounds the coil spring 42 and tube 38 at and adjacent the distal end 20 of main balloon 16. The distal engagement element 46 is a hollow, tubular structure. The distal engagement element may be formed integrally with nose piece 34 or may be bonded to the nose piece. Engagement elements 44 and 46 are formed from substantially rigid materials as, for example, from metallic materials such as stainless steel tubing. In one embodiment, the engagement elements have an outside diameter of 0.125 inches (3.175 mm) and an inside diameter of 0.105 inches (2.667 mm).

A cylindrical, generally tubular ultrasonic transducer 50 encircles the extension 26 between the stop 30 and the proximal end 18 of the main balloon, so that the ultrasonic transducer is disposed within the main balloon.

Figure 2:
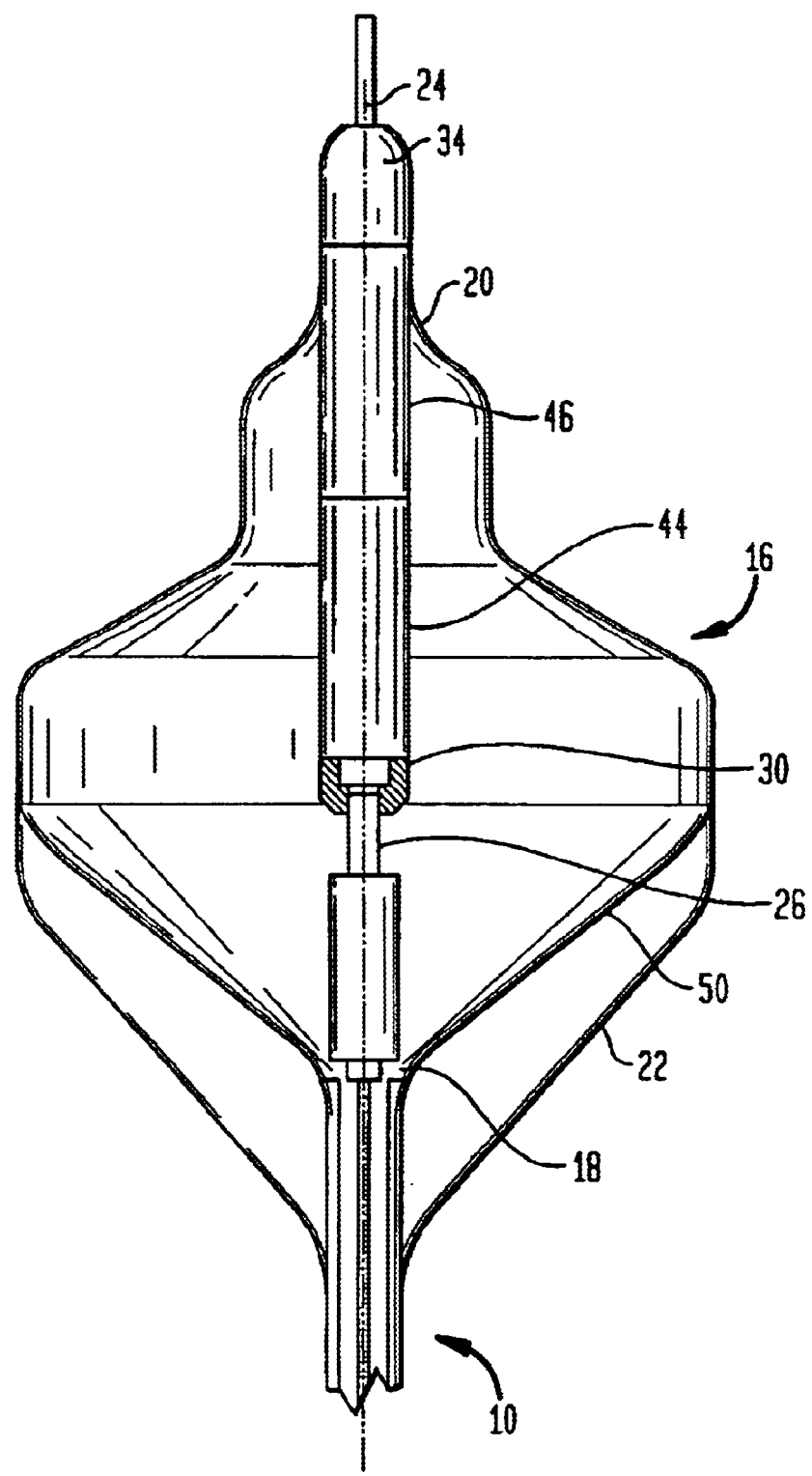
FIG. 2 is a fragmentary, diagrammatic view similar to FIG. 1 showing the device in an inflated condition.

In operation, the assembly is initially provided with the balloons deflated, so that the assembly is substantially in the condition depicted in FIG. 1. In this deflated condition, spring 42 is in a relaxed condition, whereas the balloons are in a twisted condition. An elongated element such as a guide wire 52 is threaded through the central lumen 14 of the carrier catheter through the bore 28 of extension 26, through the bore 40 of tube 38 and through the nose piece bore 36, so that the guide wire projects beyond the distal end 20 of the main balloon 16. Using conventional techniques, the guide wire is threaded into the subject as, for example, through the vascular system of the subject. Once the guide wire is in place, the carrier catheter with the balloons thereon is advanced along the guide wire and through the vascular system. During threading, the balloon assembly is substantially free to flex in radial directions, transverse to the lengthwise direction and transverse to axis 24. Because the mobile engagement elements 44 and 46 are remote from one another, at least that portion of spring 42 and tube 38 disposed in the gap between the mobile engagement elements can flex readily. Likewise, that portion of the spring and tube disposed between the proximal mobile engagement element 44 and the fixed engagement element or stop 30 can also flex.

Once the distal end of the catheter has been advanced to or near the desired location within the subject, the balloons are inflated as depicted in FIG. 2. Upon inflation, the main balloon 16 expands in radial direction, but contracts in the lengthwise or axial direction, so that the distal end 20 of the main balloon moves towards the proximal end 18 and towards the carrier catheter 10. The balloon untwists as it inflates, and hence the distal end of the balloon rotates, relative to the proximal end of the balloon, about the central axis 24. This motion compresses and twists spring 42 (FIG. 1) and shortens tube 38 in the lengthwise direction. In one embodiment, spring 42 is compressed by about 9 mm, i.e., to about 68 percent of its free length, and twisted through a full rotation (360 degrees) about central axis 24. The motion of the balloon ends towards one another also urges the mobile engagement elements 46 and 44 axially towards one another and urges the proximal mobile engagement element 44 into engagement with the fixed engagement element or stop 30, so that the assembly reaches the condition depicted in FIG. 2. The forces exerted by the balloon on the engagement elements can be substantial. In one typical embodiment, with a balloon in the inflated condition and in the configuration depicted in FIG. 2, about six pounds force is applied axially to hold the engagement elements in engagement with one another. In the inflated condition, the engagement elements abut one another so as to provide a substantially rigid column.

The rigid column formed by the engagement elements extends between the rigid extension 26 of the carrier catheter and nose piece 34. Thus, the distal end of the column is mechanically linked to the distal end of the balloon, whereas the proximal end of the column is mechanically linked to the proximal end 18 of the balloon through extension 26. The column, thus, holds the nose piece and the distal end 20 of the balloon in alignment with the axis 24 of the carrier catheter. This maintains alignment of the main balloon 16 with the ultrasonic transducer 50 and provides the optimum focusing action. While the assembly is in this condition, the guide wire 52 may be left in place or may be withdrawn and replaced with another elongated probe, catheter or guide wire. For example, a sensing device may be advanced through the bores to measure physiological conditions in the region distal to the balloon.

Ultrasonic energy may be applied by transducer 50 to ablate tissue surrounding the central axis 24 as, for example, to ablate a ring-like lesion in the wall of the heart as described more fully in the '227 application.

After completion of the desired treatment, the balloons are deflated. The spring 42 (FIG. 1) forces the proximal and distal ends of the balloons away from one another, thereby facilitating radial contraction of the balloon and returning the assembly substantially to the state illustrated in FIG. 1. The spring also returns to its relaxed, untwisted condition, so that the twisting motion about axis 24 imparted to the spring during inflation is reversed. Thus, the distal end of the spring and hence nose piece 34 and the distal end 20 of the balloon rotate relative to the proximal end of the spring about axis 24, thereby twisting the balloon around axis 24 and restoring it to substantially the original deflated condition. The axial and twisting motions aid in collapsing the balloon to a compact state. The carrier catheter and balloons are then withdrawn from the subject.

Numerous variations and combinations of the features described above can be utilized without departing from the present invention as defined by the claims. For example, the arrangement of engagement elements can be employed in structures which omit the tube 38 and which consequently omit the function of the tube in providing a passageway through the balloon. In such an arrangement, the engagement elements are guided by the spring alone, or by another flexible member provided in place of the spring. Also, the tube 38 can be formed from an ordinary material such as, for example, an elastomer or the like, which contracts or "necks" in the radial directions to a substantial extent when the tube is extended. Such an assembly is less preferred, inasmuch as the interior bore of the tube would partially or fully close when the assembly is in the deflated condition. Conversely, the preferred tubes, as discussed above, can be employed even in structures which do not incorporate the engagement elements. Also, the invention can be employed in balloon structures which do not utilize a catheter connected to the proximal end of the balloon.

Figure 3:
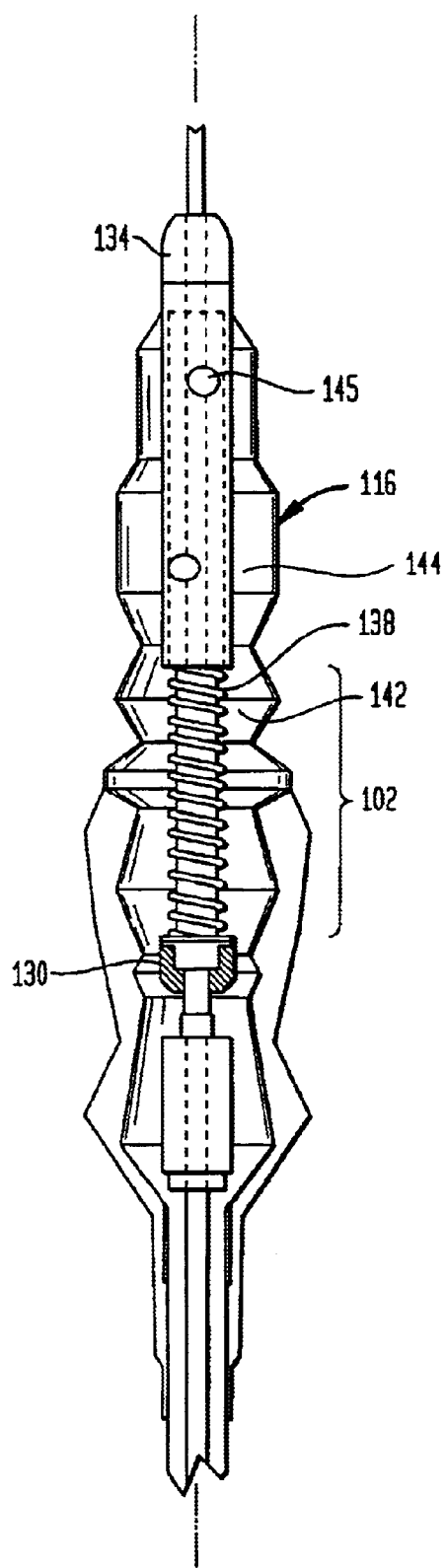
FIG. 3 is a view similar to FIG. 1 depicting a device according to a further embodiment of the invention.

The number of engagement elements can be varied. Apparatus according to a further embodiment of the invention (FIG. 3) is similar to the apparatus discussed above with reference to FIGS. 1 and 2 except that the two mobile engagement elements discussed above are replaced by a single mobile engagement element 144 which is fixed to the nose piece 134 and hence to the distal end of the balloon. This mobile engagement element is a tubular structure similar to the mobile engagement elements discussed above, and surrounds the spring 142 and tube 138. In the deflated condition shown in FIG. 3, the proximal end of mobile engagement element is remote from the fixed engagement element or stop 130. Thus, the assembly is free to flex in directions transverse to axis 124 in the gap 102 between the engagement elements. This flexibility facilitates threading of the assembly through the vascular system and removal of the assembly after treatment, in a manner similar to that discussed above. In the inflated condition, the proximal end of mobile engagement element 144 abuts the fixed engagement element or stop 130 to provide a column or support as discussed above. The assembly according to this embodiment, however, is more resistant to kinking in the deflated condition, during threading and removal.

The tubular mobile engagement element 144 is provided with one or more holes 145 extending through the wall of the tube. Holes 145 facilitate purging of air from the small space within the bore of the engagement element, immediately surrounding tube 138, when balloon 116 is filled with a liquid. Similar holes may be provided in the mobile engagement elements shown in FIGS. 1 and 2.

For example, proximal engagement element 44 can be replaced by two shorter engagement elements. Also, the proximal mobile engagement element 44 discussed above can be fixed to the fixed engagement element or stop 30.

In a further variant, where ultrasonic transducer 50 is not required or is located in a different region, stop 30 can be omitted so that the proximal engagement element abuts directly against the distal end of the catheter at the proximal end of the balloon. As discussed above, the engagement elements cooperate with the spring to limit deformation of the spring to localized areas of the spring at joints between the elements when the balloon is in an inflated condition. This effect will provide at least some increased rigidity even if the engagement elements do not abut one another, but merely approach one another in the inflated condition of the balloon.

As these and other variations and combinations of the features described above can be utilized without departing from the present invention, the foregoing description of the preferred embodiments should be taken by way of illustration rather than by limitation of the invention as defined by the claims.

What is claimed is:

1. Apparatus comprising:
    (a) a balloon having proximal and distal ends and a lengthwise direction between said ends, said balloon having an inflated condition and a deflated condition, said balloon having a deflated length between said ends in the deflated condition and an inflated length in the inflated condition, said inflated length being less than said deflated length; and
    (b) a tube disposed within said balloon and extending in the lengthwise direction of said balloon, said tube having an interior bore at least partially defining a passageway through said balloon, said tube having a proximal end mechanically linked to the proximal end of the balloon and a distal end mechanically linked to the distal end of the balloon, whereby said tube is stretched in the lengthwise direction when said balloon is deflated and shortened in the lengthwise direction when said balloon is inflated, said interior bore of said tube having diametrical dimensions which remain substantially constant despite such stretching and compression.

2. Apparatus comprising:
    (a) a balloon having proximal and distal ends and a lengthwise direction between said ends, said balloon having an inflated condition and a deflated condition, said balloon having a deflated length between said ends in the deflated condition and an inflated length in the inflated condition, said inflated length being less than said deflated length; and
    (b) a tube disposed within said balloon and extending in the lengthwise direction of said balloon, said tube having an interior bore at least partially defining a passageway through said balloon, said tube having a proximal end mechanically linked to the proximal end of the balloon and a distal end mechanically linked to the distal end of the balloon, whereby said tube is stretched in the lengthwise direction when said balloon is deflated and shortened in the lengthwise direction when said balloon is inflated, said tube being formed from a material selected from the group consisting of expanded polymers.

3. Apparatus as claimed in claim 2 wherein said tube is formed from an expanded polytetraflourethylene.

4. Apparatus as claimed in claim 1 or claim 2 wherein said bore of said tube has a first interior diameter when the balloon is deflated and the tube is shortened and a second interior diameter when the balloon is inflated and the tube is stretched, said first and second interior diameters differing from one another by less than about 20 percent of the first interior diameter.

5. Apparatus as claimed in claim 1 or claim 2 further comprising a carrier catheter mechanically linked to said proximal end of said balloon, said carrier catheter having a bore communicating with the bore of said tube.

6. Apparatus as claimed in claim 5 further comprising an elongated element extending through said carrier catheter and said bore and projecting beyond said distal end of said balloon.

7. Apparatus comprising:
(a) a balloon having proximal and distal ends and a lengthwise direction between said ends, said balloon having an inflated condition and a deflated condition, said balloon having a deflated length between said ends in the deflated condition and an inflated length in the inflated condition, said inflated length being less than said deflated length; and
(b) a plurality of engagement elements disposed at least partially within said balloon and movable with respect to one another in the lengthwise direction, said balloon urging said engagement elements into engagement with one another upon inflation of the balloon, said engagement elements being movable away from one another in the lengthwise direction upon deflation of the balloon.

8. Apparatus as claimed in claim 7 further comprising an axial member extending in the lengthwise direction within the balloon, said axial member at least partially constraining said engagement elements in radial directions transverse to said lengthwise direction.

9. Apparatus as claimed in claim 8 wherein said axial member has a proximal end mechanically linked to the proximal end of the balloon and a distal end mechanically linked to the distal end of the balloon.

10. Apparatus as claimed in claim 9 wherein said axial member includes a spring, said spring urging said ends of said balloon away from one another when said balloon is deflated.

11. Apparatus as claimed in claim 10 wherein said spring is a coil spring having an axis extending in the lengthwise direction.

12. Apparatus as claimed in claim 11 wherein at least one of said engagement elements is generally tubular and surrounds said coil spring.

13. Apparatus as claimed in claim 11 wherein said axial member further includes a tube coaxial with said coil spring and disposed within said coil spring, said tube defining an interior bore.

14. Apparatus as claimed in claim 13 further comprising a carrier catheter having a lumen, said proximal end of said balloon being secured to said carrier catheter, said lumen communicating with said interior bore of said tube.

15. Apparatus as claimed in claim 14 wherein said plurality of engagement elements include a stop secured to said carrier catheter within said balloon adjacent the proximal end thereof and a first mobile engagement element, said first mobile engagement element engaging said stop when said balloon is in said inflated condition.

16. Apparatus as claimed in claim 15 wherein said first mobile engagement element is movable in the lengthwise direction relative to said stop and said carrier catheter when said balloon is in said deflated condition.

17. Apparatus as claimed in claim 16 wherein said first mobile engagement element is mounted to the distal end of the balloon.

18. Apparatus as claimed in claim 16 wherein said engagement elements include a second mobile engagement element mounted to the distal end of the balloon and movable in the lengthwise direction relative to said first mobile engagement element and relative to said stop, said first mobile engagement element being disposed between said second mobile engagement element and said stop.

19. Apparatus as claimed in claim 15 further comprising an ultrasonic transducer mounted to said carrier catheter within said balloon and between the proximal end of the balloon and said stop.

20. A method of placing and operating a device comprising:
(a) threading a carrier catheter into the body of a mammalian subject while a balloon secured to the carrier catheter is in a deflated condition and while engagement elements disposed at least partially within the balloon are separated from one another; then
(b) inflating the balloon so that the balloon expands in radial directions and contracts in a lengthwise direction, and so that contraction of the balloon moves the engagement elements into proximity with one another;
(c) performing a procedure using the balloon in its inflated condition, said engagement elements reinforcing the balloon during said procedure; and then
(d) deflating the balloon so that said engagement elements separate from one another and withdrawing the carrier catheter and balloon while said engagement elements are separated from one another.

21. A method as claimed in claim 20 further comprising the step of urging a distal end of the balloon away from a proximal end of the balloon in a lengthwise direction during said deflating step.

22. A method as claimed in claim 21 wherein said step of urging the distal end of the balloon is performed by a spring disposed within the balloon.

23. A method as claimed in claim 22 wherein said spring twists the distal end of the balloon relative to the proximal end during the deflating step.

24. A method as claimed in claim 21 further comprising the steps of providing a guide element extending through the carrier catheter, extending through a tube disposed within the balloon and extending beyond the balloon, stretching the tube upon movement of the distal end of the balloon away from the proximal end and foreshortening the tube upon inflation of the balloon.

25. A method as claimed in claim 20 wherein said step of performing a procedure includes directing energy from a transducer disposed within the balloon to a wall of the balloon and reflecting the energy towards a target region of the subject at the wall of the balloon.

26. Apparatus as claimed in claim 7 wherein said plurality of engagement elements form a structure which substantially reinforces said balloon against lateral displacement when said balloon is in said inflated condition and said engagement elements are engaged with one another, said plurality of engagement elements permitting flexing of said balloon in lateral directions transverse to said lengthwise direction when said balloon is in said deflated condition.

27. A method as claimed in claim 20 wherein, when said balloon is in said inflated condition said engagement elements substantially reinforce said balloon against displacement in lateral direction transverse to said lengthwise direction, and said engagement elements allow flexing of said balloon in said lateral directions when said balloon is in said deflated condition.

* * * * *

UNITED STATES PATENT AND TRADEMARK OFFICE
CERTIFICATE OF CORRECTION

PATENT NO. : 6,808,524 B2
DATED : October 26, 2004
INVENTOR(S) : Patrick David Lopath and Edward Paul Harhen It is certified that error appears in the above-identified patent and that said Letters Patent is hereby corrected as shown below:

Title page,
Item [75], Inventor, "Durham, NC" should be -- Rocky Point, NY --.

Column 10,
Line 58, "direction" should read -- directions --.

Signed and Sealed this

Twenty-second Day of February, 2005

JON W. DUDAS
*Director of the United States Patent and Trademark Office*